US008321005B2

(12) United States Patent
Zhang et al.

(10) Patent No.: US 8,321,005 B2
(45) Date of Patent: Nov. 27, 2012

(54) SYSTEM FOR CONTINUOUS CARDIAC PATHOLOGY DETECTION AND CHARACTERIZATION

(75) Inventors: Hongxuan Zhang, Palatine, IL (US); Dennis Steibel, Jr., Lake Zurich, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 400 days.

(21) Appl. No.: 12/823,159

(22) Filed: Jun. 25, 2010

(65) Prior Publication Data
US 2011/0087121 A1   Apr. 14, 2011

Related U.S. Application Data

(60) Provisional application No. 61/250,921, filed on Oct. 13, 2009.

(51) Int. Cl.
*A61B 5/0402* (2006.01)
(52) U.S. Cl. ......... 600/515; 600/529; 600/509; 600/512
(58) Field of Classification Search .................. 600/509, 600/515, 529, 521
See application file for complete search history.

(56) References Cited

U.S. PATENT DOCUMENTS

| | | | |
|---|---|---|---|
| 4,850,370 A | 7/1989 | Dower | |
| 5,416,848 A | 5/1995 | Young | |
| 5,456,690 A | 10/1995 | Duong-Van | |
| 5,471,991 A | 12/1995 | Shinnar | |
| 5,588,427 A | 12/1996 | Tien | |
| 5,694,942 A | 12/1997 | Escalaona | |
| 5,758,338 A | 5/1998 | Faloutsos et al. | |
| 6,144,877 A | 11/2000 | Depetrillo | |
| 6,333,092 B1 | 12/2001 | Gipple et al. | |
| 6,422,998 B1 | 7/2002 | Vo-Dinh et al. | |
| 6,920,349 B2 * | 7/2005 | Schreck | 600/512 |
| 6,954,700 B2 | 10/2005 | Higashida et al. | |
| 6,993,377 B2 | 1/2006 | Flick et al. | |
| 7,079,681 B2 | 7/2006 | Lee et al. | |
| 7,113,931 B1 | 9/2006 | Ugajin et al. | |
| 7,565,194 B2 | 7/2009 | Tan et al. | |

OTHER PUBLICATIONS

T. Higuchi, "Approach to an irregular time series on the basis of the fractal theory", Physica D, vol. 31, 1988, p. 277-283.
Mark J. Embrechts and Y. Danon, "Determining the fractal dimension of a time series with a neural net," in Intelligent Engineering Systems through Artificial Neural Networks, C.H. Dagli, L.I. Burke, B.R. Fernandez, and J. Ghosh, Eds., ASME Press, New York,vol. 3, pp. 897-902, (1993).

* cited by examiner

*Primary Examiner* — Carl H. Layno
*Assistant Examiner* — Jon-Eric C. Morales
(74) *Attorney, Agent, or Firm* — Alexander J Burke

(57) ABSTRACT

A system determines fractal values, a nonlinear fractal ratio and fractal data patterns in a heart and maps determined fractal values to medical conditions. A system for heart performance characterization and abnormality detection includes an interface for receiving sampled data representing an electrical signal indicating electrical activity of a patient heart over at least one heart beat cycle. A signal processor calculates, a first signal characteristic value comprising a first fractal dimension value derived from the sampled data over at least a portion of a heart beat cycle, a second signal characteristic value representing a computed derivative of the first fractal dimension value and a ratio of the first and second signal characteristic values. A comparator compares the calculated ratio with a threshold value to provide a comparison indicator. A patient monitor, in response to the comparison indicator indicating the calculated signal characteristic value exceeds the threshold value, generates an alert message associated with the threshold.

22 Claims, 7 Drawing Sheets

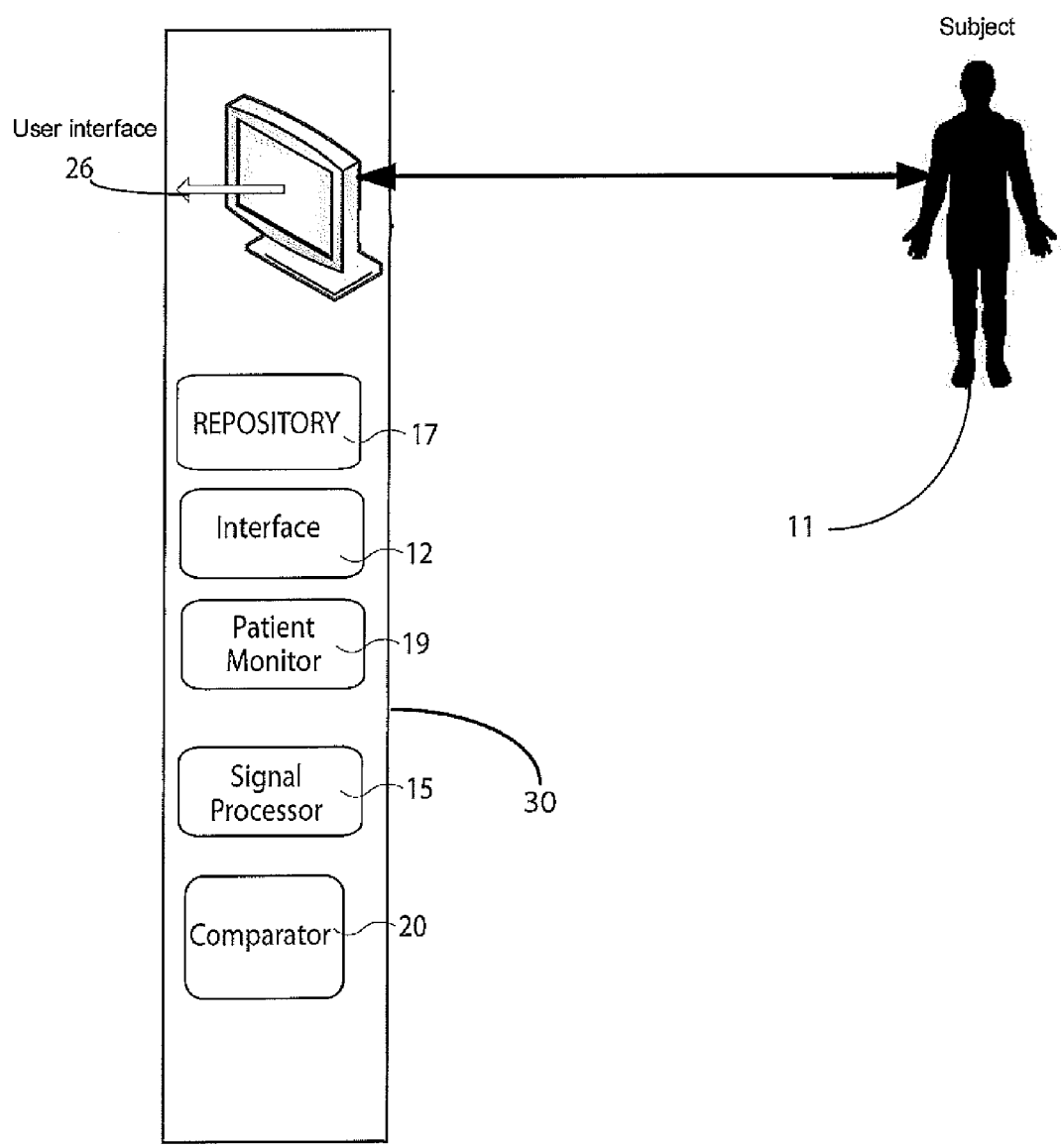

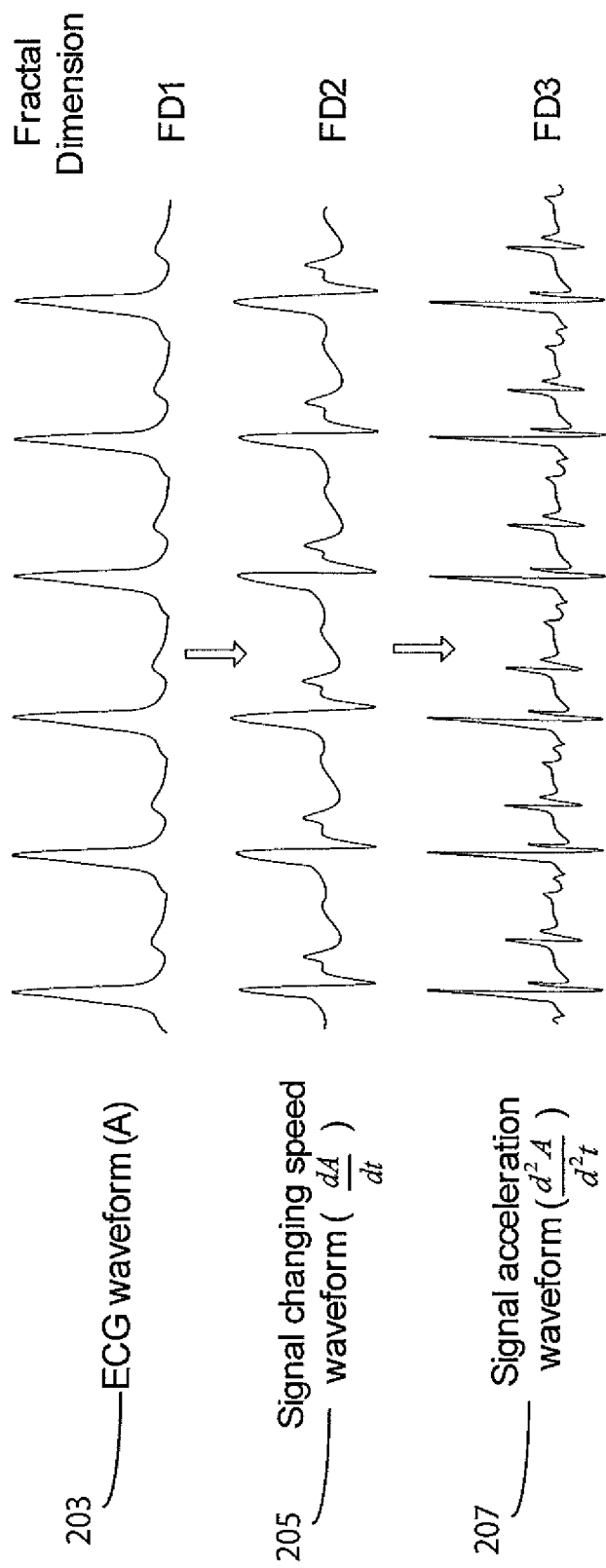

FIGURE 3

| Different kind of signals and fractal dimensions | | Signal fractal ratio |
|---|---|---|
| Time domain | 1. Signal waveform fractal: $FD1 = D(ECG\_signal\_data)$ <br> 2. Changing speed signal fractal; $FD2 = D(Speed\_signal\_data)$ $= D(\frac{dA}{dt} signal\_data\_)$ <br> 3. Accelerating signal fractal: $FD3 = D(acceleration\_signal\_data)$ $= D(\frac{d^2A}{d^2t} signal\_data)$ | $R_{12} = FD1/FD2$ <br> $R_{23} = FD2/FD3$, etc |
| Frequency domain | 1. Signal frequency (f) fractal: $fD1 = D(ECG\_frequency\_data)$ <br> 2. Frequency changing speed signal fractal; $fD2 = D(frequnecy\_Speed\_signal\_data)$ $= D(\frac{df}{dt} signal\_data\_)$ <br> 3. Accelerating signal fractal: $fD3 = D(frequency\_acceleration\_signal\_data)$ $= D(\frac{d^2f}{d^2t} signal\_data)$ | $R_{12\_f} = fD1/fD2$ <br> $R_{23\_f} = fD2/fD3$, etc |
| One or two dimensional combined signal | 1. Time vs. frequency domain fractal, including same order time and frequency fractal dimension ratios; <br> 2. Time frequency signals and data (such as wavelet time frequency analysis: TF1 is first order wavelet decomposition data series and TFi is the order I wavelet decomposition data series.) fractal: TFD1, TFD2, etc <br> $TFD1 = D(TF1\_signal\_data)$ <br> $TFD2 = D(TF2\_signal\_data)$ | $R_{1\_tf} = FD1/fD1$ <br> $R_{2\_f} = FD2/fD2$, etc <br> $R_{tf\_12} = TFD1/TFD2$, etc |

US 8,321,005 B2

SYSTEM FOR CONTINUOUS CARDIAC PATHOLOGY DETECTION AND CHARACTERIZATION

This is a non-provisional application of provisional application Ser. No. 61/250,921 filed Oct. 13, 2009, by H. Zhang et al.

FIELD OF THE INVENTION

This invention concerns a system for heart performance characterization and abnormality detection by determining a fractal dimension value from sampled data representing an electrical signal indicating electrical activity of a patient heart over at least one heart beat cycle.

BACKGROUND OF THE INVENTION

Coronary artery disease (CAD), heart-related problems and arrhythmias are serious conditions. Early arrhythmia recognition and characterization, such as of myocardial ischemia and infarction, are desirable for cardiac rhythm management to reduce cardiac disorders and irregularities. Known systems for waveform morphology and time domain parameter analysis of depolarization and repolarization, such as of a P wave, QRS complex, ST segment, T wave, for example, are used for cardiac arrhythmia monitoring and identification. However, known clinical methods, which are based on analysis of waveform morphologies and time domain parameters are often subjective and time-consuming and require expertise and clinical experience for accurate interpretation and proper cardiac rhythm management. Some known systems apply more sophisticated mathematical theories to biomedical signal interpretation, such as frequency analysis, symbolic complexity analysis and nonlinear entropy evaluation, and focus on generating a new pathology index for qualitative cardiac arrhythmia characterization. These known systems fail to provide adequate information on cardiac electrophysiological function/activity interpretation, tissue mapping and arrhythmia localization.

Known systems typically focus on time (amplitude, latency) or frequency (power, spectrum) domain changes and analysis, which fail to accurately capture and characterize small signal changes (usually undetectable in a signal waveform) in a portion (such as P wave, QRS complex, ST segment) of a heart activity representative waveform. Known systems generate false alarms and often fail to identify arrhythmia and accurately characterize ongoing cardiac events or arrhythmias. Known arrhythmia information extraction systems are often unable to qualitatively and quantitatively characterize small signal changes, and predict a pathological trend, especially in early stages of tissue malfunctioning and cardiac disorders. Known systems typically fail to analyze and identify a real time growing trend of cardiac arrhythmias, such as a pathology trend from low risk to medium, and then to high risk (severe and fatal) rhythm. Known clinical methods for cardiac arrhythmia calculation and evaluation may generate inaccurate and unreliable data and results because of unwanted noise and artifacts. Environmental noise and patient movement artifacts, such as electrical interference, can distort the waveform and make it difficult to detect R wave and ST segment elevation accurately, and even result in a false alarm. A system according to invention principles addresses these deficiencies and related problems.

SUMMARY OF THE INVENTION

A system determines fractal values, a nonlinear fractal ratio and fractal data patterns in a heart and maps determined fractal values to medical conditions to provide qualitative and quantitative interpretation of patient health status. A system for heart performance characterization and abnormality detection includes an interface for receiving sampled data representing an electrical signal indicating electrical activity of a patient heart over at least one heart beat cycle. A signal processor calculates, a first signal characteristic value comprising a first fractal dimension value derived from the sampled data over at least a portion of a heart beat cycle, a second signal characteristic value representing a computed derivative of the first fractal dimension value and a ratio of the first and second signal characteristic values. A comparator compares the calculated ratio with a threshold value to provide a comparison indicator. A patient monitor, in response to the comparison indicator indicating the calculated signal characteristic value exceeds the threshold value, generates an alert message associated with the threshold.

BRIEF DESCRIPTION OF THE DRAWING

FIG. 1 shows a system for heart performance characterization and abnormality detection, according to invention principles.

FIG. 2 illustrates cardiac signal fractal analysis for different orders of derivative of an electrophysiological signal, according to invention principles.

FIG. 3 shows a table presenting different fractal ratio analysis functions for cardiac signals, according to invention principles.

DETAILED DESCRIPTION OF THE INVENTION

Figure 4:
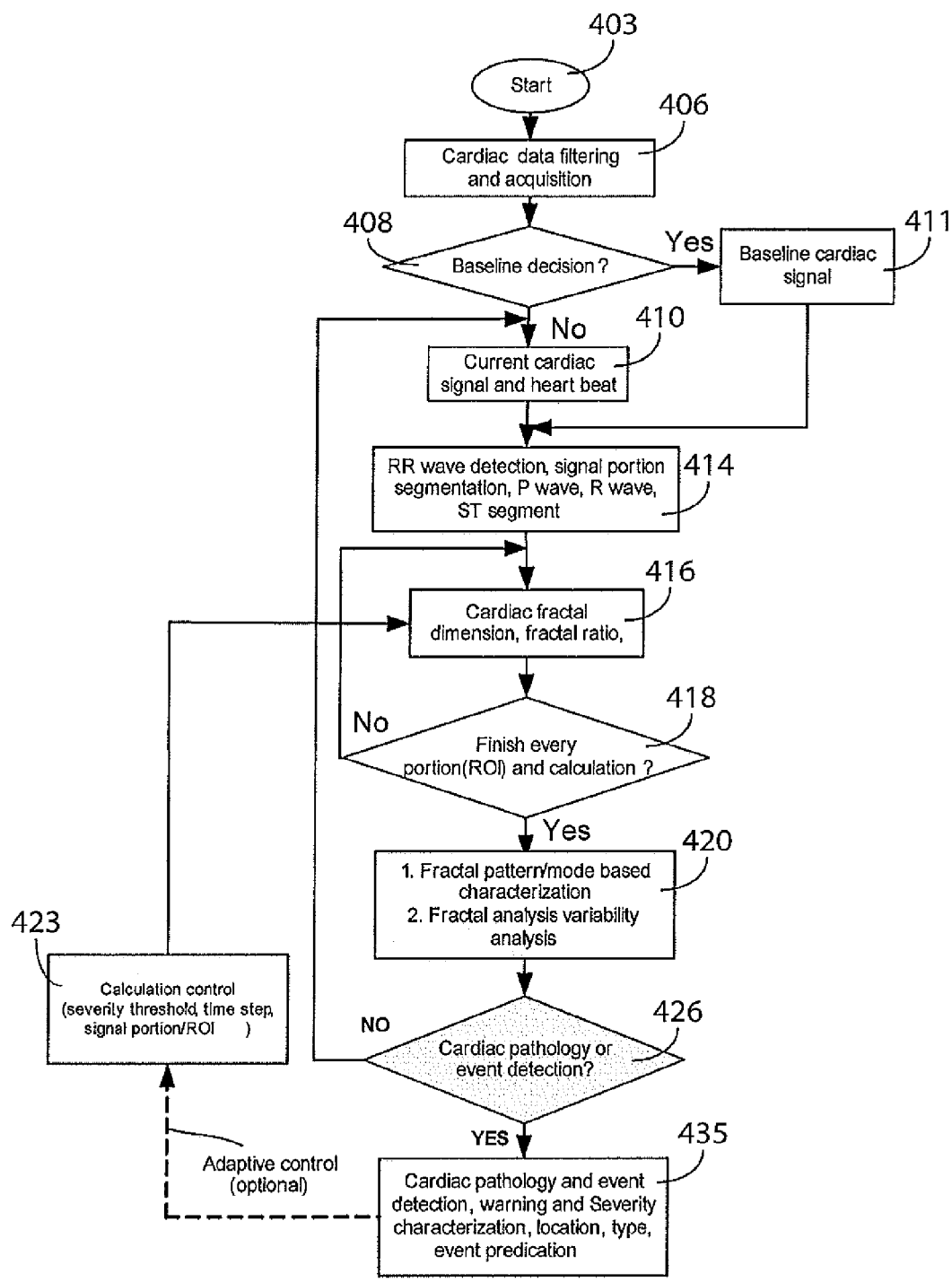
FIG. 4 shows a flowchart of a process for signal fractal ratio based cardiac condition detection, according to invention principles.

A system improves precision and reliability of detection and quantification of cardiac electrophysiological activities by analyzing and characterizing cardiac function signals (including surface ECG signals and intra-cardiac electrograms) by determining fractal values, a nonlinear fractal ratio, cardiac fractal patterns and mapping the determined data to medical conditions. The system calculates a cardiac signal fractal ratio and determines variation and distribution of the calculated ratios in a heart and associates calculated values with a time stamp (indicating time and date) and a cardiac location and severity and maps the data to medical conditions. The system differentiates between cardiac arrhythmias, characterizes pathological severity, predicts life-threatening events, and supports assessment of drug delivery and effects.

The system improves objectivity and reliability of medical electrophysiological signal analysis by extracting and characterizing arrhythmia pathology information and interpreting electrophysiological function signals such as a P wave, QRS complex, ST segment as well as repolarization and depolarization representative signals. In one embodiment the systems uses cardiac signal fractal ratio pattern analysis to indicate cardiac function and activity.

FIG. 1 shows system 10 for heart performance characterization and abnormality detection. System 10 derives fractal values and different order differential fractal values of cardiac signals. These nonlinear calculations provide improved objective, sensitive indicators to categorize clinical events and cardiac disorders. System 10 performs electrophysiological signal multi-order fractal ratio analysis and quantifies changes and variation of cardiac tissue and cardiac excitation pathways, which occur earlier than in a cardiac electrophysiological signal waveform and morphology. The system 10 electrophysiological signal fractal value and value pattern based diagnosis captures more acute and early changes and abnormality within cardiac signals and electrophysiological activities, such as of acute AF and acute ischemia events. Further, in one embodiment the cardiac signal fractal variability and pattern distribution analysis of system 10 is implemented in implantable cardiac devices. The system is also used for multi-channel cardiac electrophysiological signal diagnosis, such as of intra-cardiac signals from different leads and catheters. Additionally the cardiac signal fractal mode calculation and diagnosis may also be utilized for processing other types of signals such as oximetric signals, hemodynamic pressure signals and SPO2 blood flow signals, for example.

Cardiac tissue and cardiac pacing excitation and conduction are affected by particular abnormality and clinical events. Electrophysiological signals exhibit nonlinear abnormal variations in response to occurrence of abnormality and clinical events and reflect pacing excitation and conduction patterns as a result of a nonlinear mechanism and myocardial architecture. Changes and distortions due to clinical event and cardiac function disorders typically demonstrate nonlinear characteristics impacting signal characteristics including fractal dimension and fractal structure that area advantageously captured and characterized by fractal ratio information. System 10 identifies nonlinear heart rhythm changes and detects cardiac arrhythmias and characterizes pathological severity. System 10 employs electrophysiological signal fractal ratio value and pattern and variation analysis at multiple cardiac sites and maps derived values to medical and circulation conditions for cardiac function diagnosis in 2D and 3D. In contrast, known clinical monitoring methods (for example, detecting myocardial ischemia based on ST segment elevation exceeding 0.1 mV) may fail to provide early detection of clinical events.

System 10 comprises at least one computer system, workstation, server or other processing device 30 including interface 12, repository 17, patient monitor 19, signal processor 15, comparator 20 and a user interface 26. Interface 12 receives sampled data representing an electrical signal indicating electrical activity of a patient heart over at least one heart beat cycle. Signal processor 15 calculates a first signal characteristic value comprising a first fractal dimension value derived from the sampled data over at least a portion of a heart beat cycle, a second signal characteristic value representing a computed derivative of the first fractal dimension value and a ratio of the first and second signal characteristic values. Comparator 20 compares the calculated ratio with a threshold value to provide a comparison indicator. Patient monitor 19, in response to the comparison indicator indicating the calculated signal characteristic value exceeds the threshold value, generates an alert message associated with the threshold.

FIG. 2 illustrates cardiac signal fractal analysis for different orders of derivative of an electrophysiological signal. The system 10 (FIG. 1) fractal analysis includes determination of different order differential signals of electrophysiological signal amplitude, such as first order (signal velocity) and second order (signal acceleration). Early stage arrhythmia may not be visible in a cardiac electrogram (including a surface ECG and intra-cardiac electrogram) and corresponding signal waveforms. The small changes and artifacts are difficult to quantify using different order derivatives of signals, such as $$\frac{dA}{dt} \text{ and } \frac{d^2 A}{d^2 t}.$$

System 10 advantageously compares a fractal dimension of the different order of derivative electrophysiological signals determined at the same corresponding time in a heart cycle (i.e. having substantially the same intra-heart cycle time stamp). Thereby, nonlinear changes and distortion within the signal are amplified and easier to characterize. Waveforms 203, 205 and 207 show an ECG signal, a first order differential (velocity) of the ECG signal and a second order differential (acceleration) of the ECG signal, respectively. System 10 performs fractal analysis on waveforms 203, 205 and 207 using fractal dimension calculation of time series data (as described in the appendix) to derive fractal dimension values of waveforms 203, 205 and 207 comprising FD1, FD2 and FD3, respectively. System 10 (or a user in one embodiment) adaptively adjusts a time series based fractal dimension calculation window size, for example. In one embodiment a digital processing window of 5-10 cardiac cycles is used with an adjustable shifting time step increment. Different order derivatives of the cardiac signals are used for fractal dimension analysis including symbolized time series of the cardiac signals and frequency data of the cardiac signals.

FIG. 3 shows a table presenting different fractal ratio analysis functions for analyzing cardiac signals. System 10 employs multiple different kinds of cardiac signal waveforms and time series and differential derivatives thereof, in performing fractal dimension calculations and fractal ratio computation. The fractal ratio analysis is not limited to the functions of the table and may include different kinds of fractal ratio analysis, such as providing 1-dimensional derived signals (a symbolic data set) and 2-dimensional signals (such as a time-frequency data set). System 10 performs fractal dimension computation to calculate different derivative or integral order cardiac signal waveform data including signal velocity data $$\left(\frac{dA}{dt}\right),$$

and signal acceleration data $$\left(\frac{d^2 A}{d^2 t}\right)$$

(such as of ECG signals and ICEG signals). General fractal analysis of a signal waveform or data (which represents the overall tissue function and structure of the heart) may not be able to capture small early signal changes so system 10 determines fractal values of first and second order differentials of a signal, for example. System 10 compares the determined values against values of the patient concerned derived from corresponding signals on a previous occasion (or for corresponding signals of a patient population having similar demographic characteristics (e.g., age, weight, height, gender)).

A fractal dimension (see Appendix) comprises, $$D = \frac{\text{Log}(N(s))}{\text{Log}\left(\frac{1}{s}\right)}$$

where, D is fractal dimension value of the data series X; s is the measure of reconstructed sub data series X(m) (the measure can be length in one dimension data series, square number in a two dimension data matrix series); N(s) is the number of the reconstructed sub data series, D(•) represents a fractal calculation function. System 10 employs this fractal dimension function for different order signal data series. System 10 employs different fractal dimension calculation functions, $fD_i$ is the fractal dimension calculation function performed on frequency domain signal data of differential order i and $TF_i$ is the fractal dimension calculation function performed on joint time-frequency domain signal data of differential order i. System 10 compares different order fractal dimension changes (by computing a fractal ratio) to identify small changes within cardiac electrophysiological signals. For example, section 303 of the table of FIG. 3 shows fractal analysis functions for determining FD1, FD2 and FD3 of a signal in the time domain. Specifically, FD1 is a fractal dimension function for a signal in the time domain (ECG waveform data), FD2 is the fractal dimension function for a first order differential of the signal in the time domain (ECG velocity signal) and FD3 is the fractal dimension function for a second order differential of the signal in the time domain (ECG acceleration signal). Section 313 shows calculation of corresponding ratios of FD1 and FD2 and of FD2 and FD3.

Section 305 shows fractal analysis functions for determining fD1, fD2 and fD3 of a signal in the frequency domain. Specifically, fD1 is a fractal dimension function for a signal in the frequency domain (ECG waveform data), fD2 is the fractal dimension function for a first order differential of the signal in the frequency domain (ECG velocity signal) and fD3 is the fractal dimension function for a second order differential of the signal in the frequency domain (ECG acceleration signal). Section 315 shows calculation of corresponding ratios of fD1 and fD2 and of fD2 and fD3. Section 307 shows fractal analysis functions for determining TFD1, TFD2 and TFD3 of a signal in the time frequency domain using a wavelet decomposition function, for example. Specifically, TFD1 is a fractal dimension function for a 2 dimensional signal in the time frequency domain (ECG waveform data), TFD2 is the fractal dimension function for a first order differential of the signal in the time frequency domain (ECG velocity signal) and TFD3 is the fractal dimension function for a second order differential of the signal in the time frequency domain (ECG acceleration signal). Section 317 shows calculation of corresponding ratios of TFD1 and TFD2 and of TFD2 and TFD3.

System 10 calculates a fractal ratio that is automatically or manually selected in response to data identifying a clinical application. The fractal analysis and ratio calculation captures and quantifies nonlinear changes within cardiac signals. The fractal analysis is not limited to analysis of one or more whole hear beat cycles (such as by using a single or multi-beat calculation time window). System 10 is usable for analyzing a particular portion of a signal, such as P wave or a QRS complex for beat to beat arrhythmia testing and detection.

FIG. 4 shows a flowchart of a process performed by system 10 (FIG. 1) for signal fractal ratio based cardiac condition detection. The system calculates different kinds of signal fractal ratio (as shown in FIG. 3) for continuously monitoring cardiac signal variation and distortion to detect clinical events. The different kinds of fractal ratios facilitate identification of different kinds of cardiac malfunctions or arrhythmias, such as myocardial ischemia and atrial fibrillation. System 10 analyzes values of different derivative (or integral) order of a signal fractal dimension and ratio (including a fractal nonlinear pattern, ratio, deviation and variation) to determine the location, timing, severity, type of the cardiac pathology and disease, earlier and more accurately.

Following the start at step 403, interface 12 in step 406 filters received sampled data representing an electrical (electrophysiological) signal indicating electrical activity of a patient heart over at least one heart beat cycle using a filter adaptively selected in response to data indicating clinical application (e.g. ischemia detection, rhythm analysis application) and in step 408 determines whether a baseline level has already been determined for a current filtered signal 410. If a baseline level has not been selected, a baseline cardiac signal level is selected in step 411 by interface 12.

In step 414, signal processor 15 identifies different segments (QRS, ST, P wave, Q wave, R wave, S wave, ST segment, T wave, U wave segments, for example) of the filtered electrophysiological signal. In step 416, signal processor 15 calculates a first signal characteristic value comprising a first fractal dimension value derived from the sampled data over at least a portion of a heart beat cycle, a second signal characteristic value representing a computed derivative of the first fractal dimension value and a ratio of the first and second signal characteristic values. The calculations are iteratively performed in step 416 for different portions of a single heart cycle and for multiple heart cycles for a region of interest (ROI) via step 418 until the desired signal portions are completed. Processor 15 performs real time data based cardiac signal data (including different order signals, such as speed data and acceleration data) fractal calculation, including time domain signal fractal dimension and ratio, frequency domain data dimension and ratio as shown in FIG. 3. Processor 15 in step 420 identifies a cardiac signal fractal pattern comprising calculated fractal values for each stage (portion) in a region of interest (ROI) of a heart cycle for a whole signal cycle and determines fractal value variation and rate of variation.

In step 426 signal processor 15 employs mapping information, associating ranges of a calculated fractal value or values derived from the fractal value (including fractal ratios as shown in FIG. 3), with corresponding medical conditions (e.g., arrhythmias) in determining patient medical conditions, events and patient health status. If signal processor 15 and comparator 20 in step 426 determine a medical condition indicating cardiac impairment or another abnormality is identified, patient monitor 19 in step 435 generates an alert message identifying the medical condition and abnormality and communicates the message to a user. Processor 15 also determines the severity and location of the condition. Processor 15 in step 423 adaptively adjusts calculation time step, the selected portions and ROI of a filtered signal analyzed and adjusts a threshold employed by comparator 20 to improve medical condition detection. If signal processor 15 and comparator 20 in step 426 do not identify a medical condition, the process is repeated from step 410. System 10 identifies and monitors different kinds of clinical events and cardiac pathology, including atrial fibrillation, ventricular tachycardia, and chamber to chamber fractal structure comparison using a calculated signal fractal ratio and ratio variation.

Figure 5:
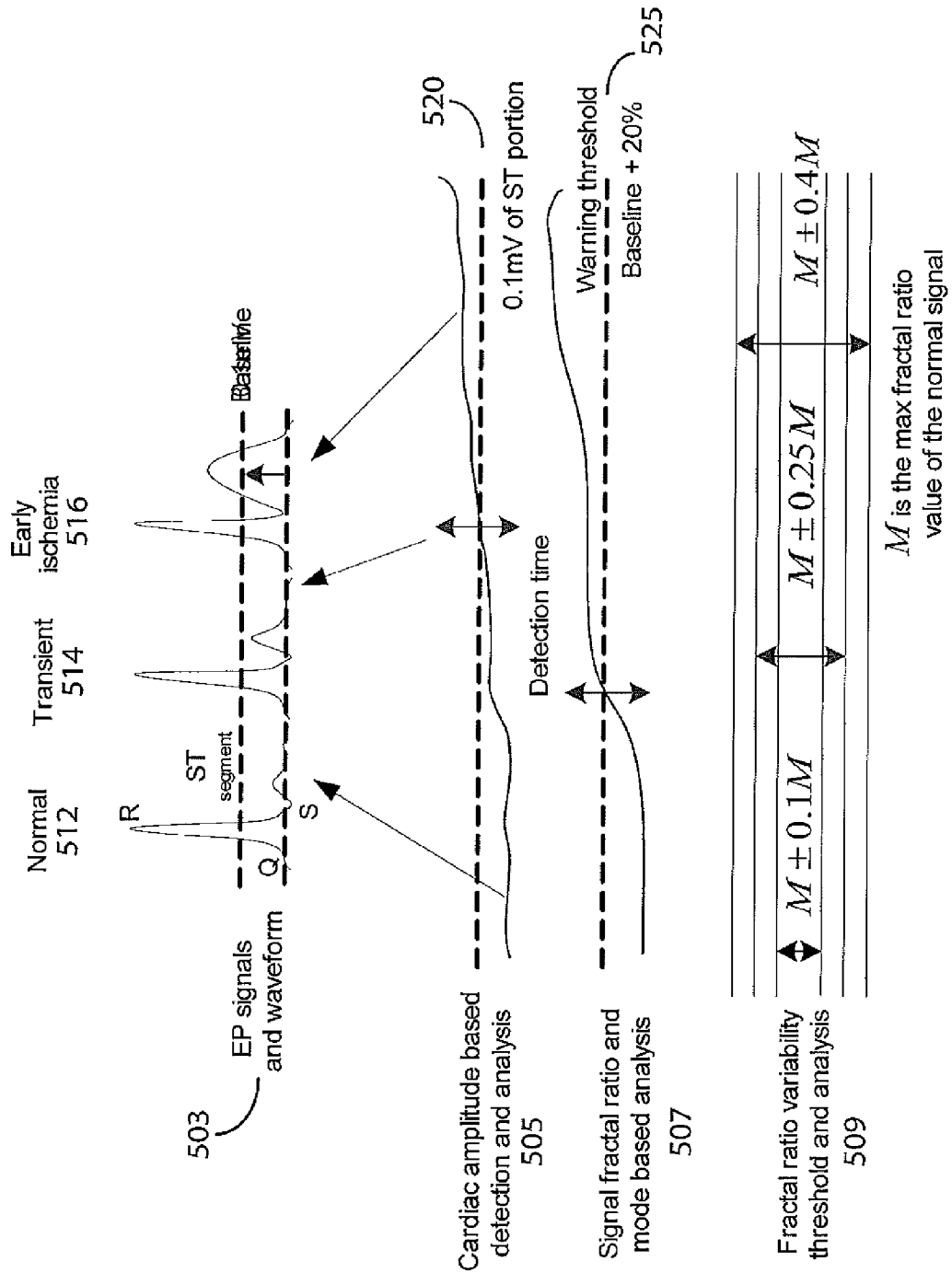
FIG. 5 illustrates use of a calculated fractal value for ischemia analysis, tracking and characterization, according to invention principles.

FIG. 5 illustrates use of a calculated fractal value for ischemia analysis, tracking and characterization. System 10 (FIG. 1) performs a fractal ratio and fractal ratio variation based ischemia analysis, to identify acute myocardial ischemia by quantifying nonlinear structure changes within cardiac signals, cardiac functions and heart structures (such as electrophysiological pathways). The fractal ratio analysis is utilized in different kinds of arrhythmia analysis to provide an objective diagnosis.

A system acute ischemia event and signal energy calculation is shown in FIG. 5 presenting different episodes, from healthy (normal) to intermediate (transient), to early ischemia. If relying on the EP signal amplitude (voltage) change, such as ST segment (0.1 mV change), a clinical user may need 20-30 minutes before a warning of detected ST segment elevation. In contrast the signal fractal mode analysis provides early analysis and an index for a user to track myocardial function and perfusion procedure deviation, which results from cardiac excitation function variation or myocardial muscle pathology, for example. In FIG. 5 different methods are compared, including known clinical gold standard (0.1 mV elevation of ST segment), fractal ratio (e.g. using fractal ratio R12 of FIG. 3) of a whole heart cycle and fractal ratio deviation monitoring using a comparison threshold.

An acute ischemia event and fractal ratio and variation tracking are illustrated in FIG. 5 which shows different episodes, including healthy (normal) 512, intermediate (transient) 514 and early ischemia 516 episodes. Detection of an electrophysiological signal amplitude (voltage) change for detection of a cardiac impairment, such as an ST segment (0.1 mV) change may take 20-30 minutes. In contrast, the system 10 signal fractal analysis provides early detection enabling a user to track cardiac function. An acute ischemic event may occur a substantial time before an ST segment waveform 505 elevation exceeds a 0.1 mV threshold 520 for ischemic event warning. The electrograms in episode 514 (transient ischemia) have shown little change while this change is magnified and quantified using fractal ratio analysis.

The small transient ischemia episode 514 in electrophysiological signal 503 comprising an ST segment change (a trend) is detected and quantitatively characterized using fractal analysis. The fractal ratio is plotted in waveform 507 with accompanying detection variability thresholds 509. System 10 detects transient ischemia 514 in fractal ratio waveform 507 using a threshold 525 set at waveform 507 baseline value plus 20% (with baseline value normalized as 1). Threshold 525 is adaptively and dynamically set in response to patient and signal quality characteristics (such as noise, artifact effect). For example, when the signal to noise ratio is 10:1, the threshold is set at 20% or more, while a threshold is set at 30% or more when the signal to noise ratio is 5:1 or less. The threshold is selected in response to sensitivity and stability of arrhythmia detection and quantification as indicated by a statistical analysis (such as a T test) to achieve a 95% confidence in detection of clinical events.

Figure 6:
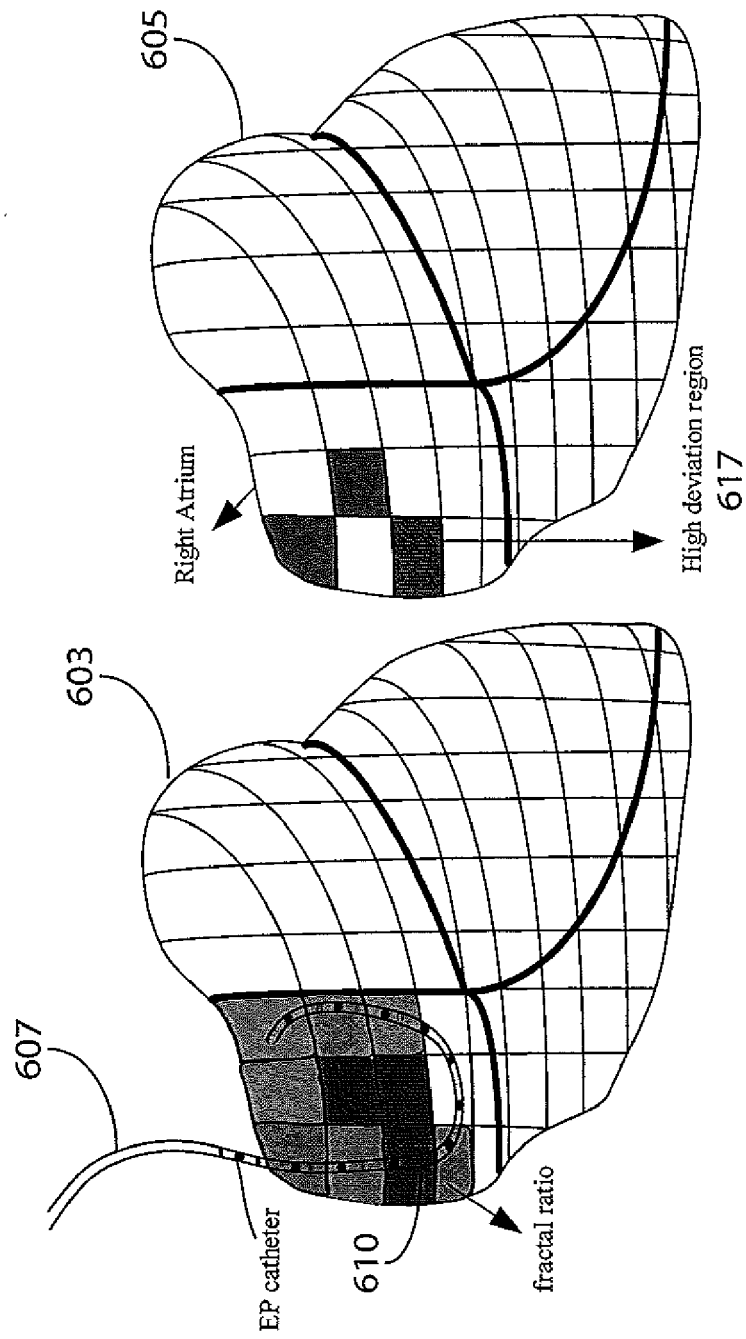
FIG. 6 illustrates cardiac pattern recognition and analysis based on signal fractal ratio analysis, according to invention principles.

FIG. 6 illustrates cardiac pattern recognition and analysis based on signal fractal ratio analysis. Fractal ratio and fractal ratio variation values are mapped to medical conditions in real time using a repository of mapping information associating ranges of fractal ratio and ratio variation with corresponding medical conditions. Fractal values are mapped for 2D and 3D cardiac electrophysiological activity tracking. Diagram 603 shows multi-channel intra-cardiac electrogram (ICEG) catheter 607 concurrently sensing electrophysiological (EP) signals from multiple sites within a heart right atrium for recording by system 10. Signal processor 15 calculates fractal ratio and fractal ratio variation values at different sites such as site 610 and maps calculated values to one or more abnormal tissue sites and detects arrhythmias to facilitate prevention of life threatening events. Diagram 605 illustrates tissue regions such as region 617 having calculated fractal variation values and standard deviation patterns exceeding a predetermined threshold. The multi-channel (channel number and spatial resolution depend on lead numbers of invasive catheters) real time fractal ratio and variation provide different kinds of 3D information for mapping including, 1) fractal dimension and ratio information and complexity pattern information and 2) fractal values and deviation patterns (a singularity is usually utilized to track the acute cardiac event with abrupt changes). System 10 maps an electrophysiological signal fractal ratio to tissue structure distortion indicators and cardiac function indicators.

In one embodiment, system 10 uses color in diagrams 603 and 605 to indicate severity of cardiac pathology and events for use in determining a sequence and priority of medical treatment and drug delivery. The abnormal tissue location and arrhythmia severity, are visually mapped to facilitate treatment determination by a clinician. The cardiac signal fractal ratio and value distribution analysis uses surface ECG signal and other kinds of electrophysiological signals, such as ICEG signals (intra-cardiac electrograms) and hemodynamic pressure signals (such as IBP, NIBP signals, cardiac output signals) and may be used within a pacemaker and cardiac implantable device for measurement and characterization of patient cardiac pathology and arrhythmia.

Figure 7:
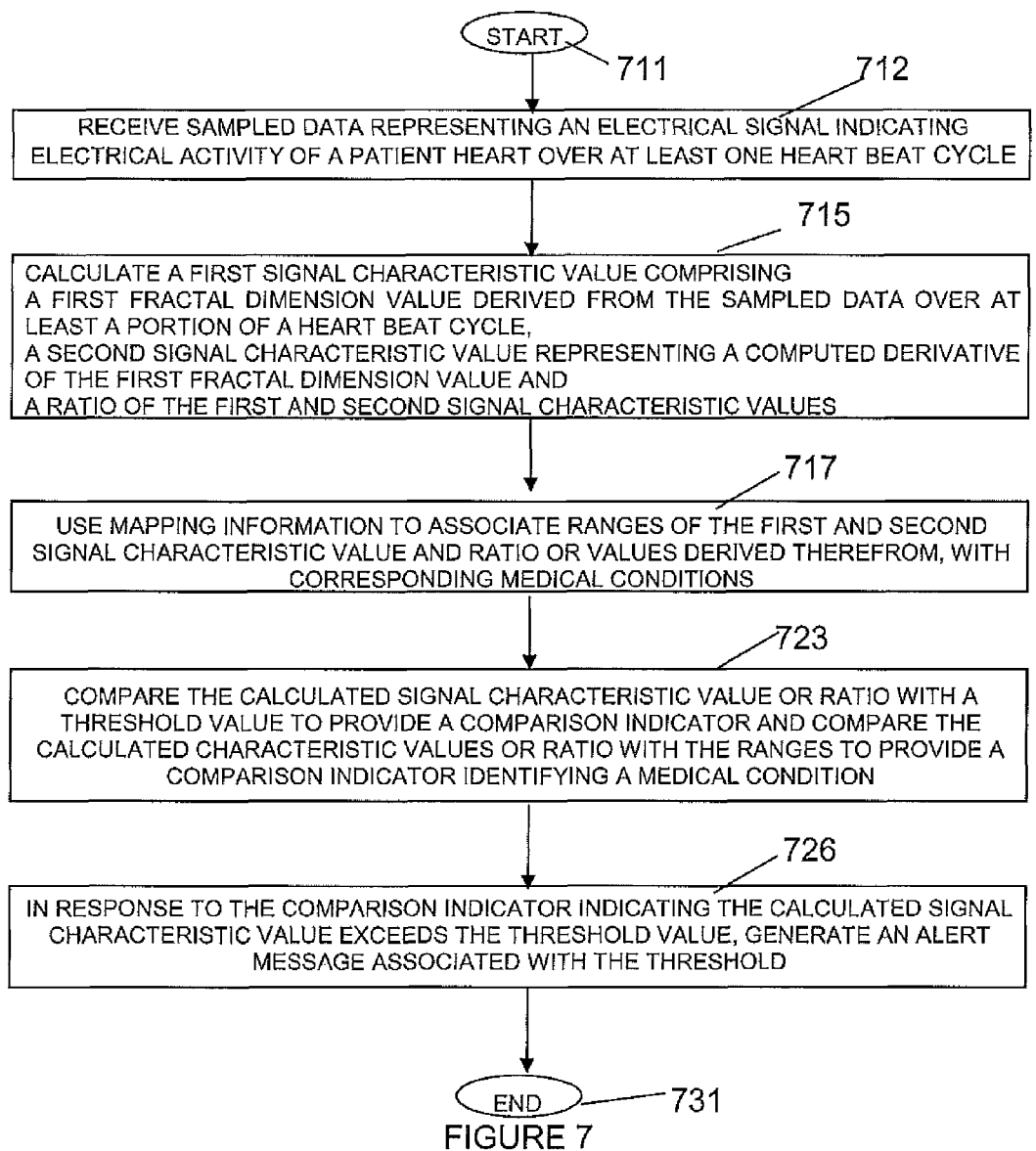
FIG. 7 shows a flowchart of a process used by a system for heart performance characterization and abnormality detection, according to invention principles.

FIG. 7 shows a flowchart of a process used by system 10 for heart performance characterization and abnormality detection. In step 712 following the start at step 711, interface 12 receives a digitized electrical signal comprising sampled data representing an electrical signal indicating electrical activity of a patient heart, as well as frequency content of the electrical signal and composite time and frequency content of the electrical signal indicating electrical activity of a patient heart over at least one heart beat cycle. Signal processor 15 in step 715 calculates, a first signal characteristic value comprising a first fractal dimension value derived from the sampled data over at least a portion of a heart beat cycle, a second signal characteristic value representing a computed derivative of the first fractal dimension value and a ratio of the first and second signal characteristic values.

In one embodiment, signal processor 15 calculates the ratio for a predetermined portion (such as an ST segment) of a heart beat cycle in response to a synchronization signal and calculates at least one of the first and second signal characteristic values as an averaged value over multiple heart beat cycles and in response to a heart rate synchronization signal. In another embodiment, signal processor 15 calculates first and second signal characteristic values for a first and different second portion of a single heart cycle respectively and calculates a ratio of the first and second signal characteristic values for the first and different second portion of the single heart cycle. The first and different second portion of the single heart cycle correspond to repolarization and depolarization segments respectively. In a further embodiment, signal processor 15 calculates signal characteristic values for the same portion of different first and second heart cycles and calculates a ratio of the signal characteristic values for the same portion of different first and second heart cycles. Also signal processor 15 calculates the first fractal dimension value D as, $$D = \frac{\text{Log}(N(s))}{\text{Log}\left(\frac{1}{s}\right)}$$

where, D is fractal dimension value of sampled data series X; s is a measure of a reconstructed sub data series X(m) (the measure can be length in one dimension data series, square number in two dimension data matrix series), N(s) is the number of the reconstructed sub data series.

In step 717, signal processor 15 uses predetermined mapping information to associate ranges of the first and second signal characteristic value and ratio or values derived therefrom, with corresponding medical conditions. The predetermined mapping information associates ranges of the ratio with particular patient demographic characteristics and with corresponding medical conditions and the system uses patient demographic data including at least one of, age weight, gender and height in comparing the ratio with the ranges (of the particular patient concerned or of a demographically compatible population of patients) and generating an alert message indicating a potential medical condition. In step 723, comparator 20 compares the calculated ratio with a threshold value to provide a comparison indicator and compares the ratio with the ranges to provide a comparison indicator identifying a medical condition. Signal processor 15 dynamically adjusts the threshold value in response to a determined sensitivity of arrhythmia detection. The threshold value is derived from recorded electrical signal data for the patient or for a population of patients that has similar demographic characteristics including at least two of, (a) age, (b) weight, (c) gender and (d) height, to those of the patient.

In step 726 patient monitor 19 substantially continuously monitors the comparison indicator for at least a 24 hour period. In response to the comparison indicator indicating the calculated signal characteristic value exceeds the threshold value, patient monitor 19 generates an alert message associated with the threshold. Patient monitor 19, in response to the comparison indicator indicating the calculated signal characteristic value lies in a predetermined value range, generates an alert message associated with the value range and identifying the medical condition. The process of FIG. 7 terminates at step 731.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example, and is conditioned using executable instructions to perform special purpose functions not performed by a general purpose computer. A processor may be coupled (electrically and/or as comprising executable components) with any other processor enabling interaction and/or communication there-between. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-7 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system analyzes cardiac function signals by determining fractal values, a nonlinear fractal ratio, fractal value variation and 3D cardiac fractal patterns and associates calculated values with a time stamp (indicating time and date) and a cardiac location and severity and maps the data to medical conditions. Further, the processes and applications may, in alternative embodiments, be located on one or more (e.g., distributed) processing devices on a network linking the units of FIG. 1. Any of the functions and steps provided in FIGS. 1-7 may be implemented in hardware, software or a combination of both.

Appendix

Fractal Dimension Concept and Calculation for Waveform and Data Series

Different methods are usable to define and calculate the fractal dimension, such as fractal structure based fractal dimension and Rényi entropy based fractal dimension. Here a time data series reconstruction based embedded fractal dimension calculation is used.

Consider a finite set of time series observations taken at a regular interval (such as minimum data sampling time):

X(1), X(2), X(3), . . . , X(N),

From the given time series, a new time series can be constructed, $X_k^m$, defined as follows:

$$X(m), X(m+k), X(m+2k), \ldots , X\left(m + \left[\frac{N-m}{k}\right] \cdot k\right),$$

$$(m = 1, 2, \ldots k)$$

Where [ ] denotes the Gauss' notation and both k and m are integers. m and k indicate the initial time and the interval time, respectively. For a time interval equal to k, k sets of new time series can be derived. In the case of k=3 and N=100, three time series obtained by the above process are described as following:

$X_3^1$: X(1), X(4), X(7), ...
$X_3^2$: X(2), X(5), X(8), ...
$X_3^3$: X(3), X(6), X(9), ...

Defining the length of the curve, $X_k^m$, as following:

$$L_m(k) = \left\{ \left( \sum_{i=1}^{[\frac{N-M}{k}]} |X(m+ik) - X(m+(i-1)\cdot k)| \right) \cdot \frac{N-1}{\left[\frac{N-m}{k}\right]\cdot k} \right\} / k$$

In which N−1/[(N−m)/k]·k represents the normalization factor of the curve length of the subset time series. The length of the curve for the time interval k, <L(k)>, is defined as the average value over k sets of $L_m(k)$. If <L(K)>∝$K^{-D}$, then the curve is fractal with the dimension D. (with the reconstructed time series data, by using logarithm the fractal dimension is calculated)

What is claimed is:

1. A system for heart performance characterization and abnormality detection, comprising:
   an interface for receiving sampled data representing an electrical signal indicating electrical activity of a patient heart over at least one heart beat cycle;
   a signal processor for calculating,
      a first signal characteristic value comprising a first fractal dimension value derived from said sampled data over at least a portion of a heart beat cycle,
      a second signal characteristic value representing a computed derivative of said first fractal dimension value and
      a ratio of the first and second signal characteristic values;
   a comparator for comparing the calculated ratio with a threshold value to provide a comparison indicator; and
   a patient monitor for in response to said comparison indicator indicating the calculated signal characteristic value exceeds the threshold value, generating an alert message associated with the threshold.

2. A system according to claim 1, wherein
said patient monitor, in response to said comparison indicator indicating the calculated signal characteristic value lies in a predetermined value range, generates an alert message associated with the value range.

3. A system according to claim 2, wherein
said patient monitor substantially continuously monitors said comparison indicator for at least a 24 hour period.

4. A system according to claim 1, wherein
said threshold value is derived from recorded electrical signal data for said patient.

5. A system according to claim 1, wherein
said threshold value is derived from recorded electrical signal data for a population of patients.

6. A system according to claim 5, wherein
said population of patients has similar demographic characteristics including at least two of, (a) age, (b) weight, (c) gender and (d) height, to those of said patient.

7. A system according to claim 1, wherein
said signal processor dynamically adjusts said threshold value in response to a determined sensitivity of arrhythmia detection.

8. A system according to claim 1, wherein
said signal processor calculates said ratio for a predetermined portion of a heart beat cycle in response to a synchronization signal.

9. A system according to claim 8, wherein
said predetermined portion of said heart beat cycle includes an ST segment.

10. A system according to claim 1, wherein
said signal processor calculates at least one of the first and second signal characteristic values as an averaged value over a plurality of heart beat cycles.

11. A system according to claim 1, wherein
said signal processor calculates the first and second signal characteristic values in response to a heart rate synchronization signal.

12. A system according to claim 1, including
a repository of mapping information, associating ranges of the ratio with corresponding medical conditions and
said comparator compares the ratio with said ranges to provide a comparison indicator identifying a medical condition and
said patient monitor generates an alert message identifying said medical condition.

13. A system according to claim 12, wherein
said predetermined mapping information associates ranges of the ratio with particular patient demographic characteristics and with corresponding medical conditions and
said system uses patient demographic data including at least one of, age weight, gender and height in comparing the ratio with said ranges and generating an alert message indicating a potential medical condition.

14. A system according to claim 1, wherein
said interface provides a digitized electrical signal and
said signal processor calculates the first and second signal characteristic values of the digitized electrical signal.

15. A system according to claim 1, wherein
said signal processor calculates said first fractal dimension value D as, $$D = \frac{\text{Log}(N(s))}{\text{Log}\left(\frac{1}{s}\right)}$$

where, D is fractal dimension value of sampled data series X; s is a measure of a reconstructed sub data series X(m) (the measure can be length in one dimension data series, square number in two dimension data matrix series), N(s) is the number of the reconstructed sub data series.

16. A system according to claim 1, wherein
said signal processor calculates first and second signal characteristic values for a first and different second portion of a single heart cycle respectively and
said signal processor calculates a ratio of the first and second signal characteristic values for the first and different second portion of the single heart cycle.

17. A system according to claim 16, wherein
the first and different second portion of the single heart cycle correspond to repolarization and depolarization segments respectively.

18. A system according to claim 1, wherein
said signal processor calculates signal characteristic values for the same portion of different first and second heart cycles.

19. A system according to claim 18, wherein
said signal processor calculates a ratio of the signal characteristic values for the same portion of different first and second heart cycles.

20. A system for heart performance characterization and abnormality detection, comprising:
an interface for receiving sampled data representing frequency content of an electrical signal indicating electrical activity of a patient heart over at least one heart beat cycle;
a signal processor for calculating,
  a first signal characteristic value comprising a first fractal dimension value derived from said sampled data over at least a portion of a heart beat cycle,
  a second signal characteristic value representing a computed derivative of said first fractal dimension value and
  a ratio of the first and second signal characteristic values;
a comparator for comparing the calculated ratio with a threshold value to provide a comparison indicator; and
a patient monitor for in response to said comparison indicator indicating the calculated signal characteristic value exceeds the threshold value, generating an alert message associated with the threshold.

21. A system for heart performance characterization and abnormality detection, comprising:
an interface for receiving sampled data representing composite time and frequency content of an electrical signal indicating electrical activity of a patient heart over at least one heart beat cycle;
a signal processor for calculating,
  a first signal characteristic value comprising a first fractal dimension value derived from said sampled data over at least a portion of a heart beat cycle,
  a second signal characteristic value representing a computed derivative of said first fractal dimension value and
  a ratio of the first and second signal characteristic values;
a comparator for comparing the calculated ratio with a threshold value to provide a comparison indicator; and
a patient monitor for in response to said comparison indicator indicating the calculated signal characteristic value exceeds the threshold value, generating an alert message associated with the threshold.

22. A method for heart performance characterization and abnormality detection, comprising the activities of:
receiving sampled data representing an electrical signal indicating electrical activity of a patient heart over at least one heart beat cycle;
calculating,
  a first signal characteristic value comprising a first fractal dimension value derived from said sampled data over at least a portion of a heart beat cycle,
  a second signal characteristic value representing a computed derivative of said first fractal dimension value and
  a ratio of the first and second signal characteristic values;
comparing the calculated ratio with a threshold value to provide a comparison indicator; and
in response to said comparison indicator indicating the calculated signal characteristic value exceeds the threshold value, generating an alert message associated with the threshold.

* * * * *